(12) United States Patent
Oberhoffner et al.

(10) Patent No.: US 10,124,086 B2
(45) Date of Patent: Nov. 13, 2018

(54) COMPOSITION, MOLDED ARTICLE, THREAD, MEDICAL KIT AND MEDICAL PRODUCT WITH IMPROVED DEGRADATION PROFILE

(71) Applicant: ITV Denkendorf Produktservice GmbH, Denkendorf (DE)

(72) Inventors: Sven Oberhoffner, Weinstadt (DE); Erhard Müller, Stuttgart (DE)

(73) Assignee: ITV Denkendorf Produktservice GmbH (DE)

( * ) Notice: Subject to any disclaimer, the term of this patent is extended or adjusted under 35 U.S.C. 154(b) by 355 days.

(21) Appl. No.: 14/394,804

(22) PCT Filed: Mar. 28, 2013

(86) PCT No.: PCT/EP2013/056752
§ 371 (c)(1),
(2) Date: Oct. 16, 2014

(87) PCT Pub. No.: WO2013/156293
PCT Pub. Date: Oct. 24, 2013

(65) Prior Publication Data
US 2015/0100086 A1    Apr. 9, 2015

(30) Foreign Application Priority Data

Apr. 18, 2012 (DE) .................. 10 2012 206 400

(51) Int. Cl.
| | | |
|---|---|---|
| A61L 17/10 | (2006.01) | |
| A61L 27/18 | (2006.01) | |
| A61L 27/50 | (2006.01) | |
| A61L 27/58 | (2006.01) | |
| A61L 31/12 | (2006.01) | |
| A61L 31/14 | (2006.01) | |
| A61B 17/06 | (2006.01) | |

(52) U.S. Cl.
CPC ...... *A61L 17/105* (2013.01); *A61B 17/06166* (2013.01); *A61L 27/18* (2013.01); *A61L 27/505* (2013.01); *A61L 27/58* (2013.01); *A61L 31/128* (2013.01); *A61L 31/143* (2013.01); *A61L 31/148* (2013.01)

(58) Field of Classification Search
CPC .............. A61F 2/90; A61F 2210/0004; A61F 2220/0075; A61K 47/48992
See application file for complete search history.

(56) References Cited

U.S. PATENT DOCUMENTS

| | | | | |
|---|---|---|---|---|
| 4,052,988 | A | * 10/1977 | Doddi | A61B 17/06166 528/354 |
| 4,201,216 | A | 5/1980 | Mattei | |
| 4,444,927 | A | 4/1984 | Borysko | |
| 4,532,929 | A | * 8/1985 | Mattei | A61L 17/145 427/2.31 |
| 6,005,019 | A | 12/1999 | Liu | |
| 6,206,908 | B1 | 3/2001 | Roby | |
| 6,616,687 | B1 | * 9/2003 | Tomihata | A61L 17/145 606/228 |
| 2009/0048627 | A1 | * 2/2009 | Hadba | A61B 17/06166 606/228 |
| 2009/0254104 | A1 | * 10/2009 | Murray | A61K 38/39 606/151 |
| 2010/0211098 | A1 | 8/2010 | Hadba et al. | |
| 2012/0059413 | A1 | 3/2012 | Calero et al. | |

FOREIGN PATENT DOCUMENTS

| | | |
|---|---|---|
| CN | 101 152 588 | 4/2008 |
| DE | 27 55 344 | 6/1978 |
| DE | 10 210 034 471 | 2/2012 |
| EP | 0 170 966 | 2/1986 |
| EP | 2 415 488 | 2/2012 |
| WO | 2007/100575 | 9/2007 |

OTHER PUBLICATIONS

German Search Report dated Oct. 23, 2012 from corresponding German Application No. 102012206400.1.
Andjelic et al., "Crystallization Study on Absorbable Poly (p-Dioxanone) Polymers by Differential Scanning Calorimetry", *Journal of Applied Polymer Science*, 2001, vol. 79, pp. 742-759.
Sabino et al., "Influence of in Vitro Hydrolytic Degradation on the Morphology and Crystallization Behavior of Poly (p-dioxanone)", American Chemical Society, 2004, vol. 5, pp. 358-370.

* cited by examiner

*Primary Examiner* — Gregory Listvoyb
(74) *Attorney, Agent, or Firm* — DLA Piper LLP (US)

(57) ABSTRACT

A composition includes polydioxanone and/or a copolymer thereof and at least one carboxylic salt. A molding includes the composition. A thread includes the composition. A medical kit includes the composition and a medical product includes the composition.

17 Claims, No Drawings

COMPOSITION, MOLDED ARTICLE, THREAD, MEDICAL KIT AND MEDICAL PRODUCT WITH IMPROVED DEGRADATION PROFILE

TECHNICAL FIELD

This disclosure relates to a composition comprising polydioxanone and/or a copolymer thereof, to a molding comprising the composition, to a thread comprising the composition, to a medical kit comprising the composition and to a medical product comprising the composition.

BACKGROUND

Polydioxanone (PDO) is an absorbable, synthetic polymer having numerous possible medical uses.

Compared to polyglycolide and polylactide, polydioxanone has the fundamental advantage of greater flexibility (lower flexural stiffness), and it is for this reason that monofil surgical suture materials are manufactured therefrom and used.

Compared to polyglycolide and copolymers thereof, polydioxanone additionally exhibits slowed hydrolytic degradation, which is particularly advantageous especially in indications with retarded wound healing.

Important determinants for the degradation characteristics of polydioxanone are the morphology and crystallinity thereof.

It is known that the crystallinity and crystallization rate of p-dioxanone-containing copolymers are reduced compared to the homopolymer ("Crystallization Study on Absorbable Poly(p-dioxanone) Polymers by Differential Scanning calorimetry"; Andjelic et al.: Journal of Applied Polymer Science, vol. 79, 742-759 (2001)).

It is also known that hydrolytic degradation in polydioxanone proceeds almost in two stages, in that amorphous regions are subject to quicker hydrolytic degradation than the crystalline regions ("Influence of in vitro Hydrolytic Degradation on the Morphology and Crystallization Behaviour of Poly(p-dioxanone)"; Sabino et al.: Biomacromolecules 2004, 5, 358-370)).

It is additionally known that addition of inorganic materials such as calcium carbonate, β-tricalcium phosphate and calcium sulfate or boron nitrite, talc or hydroxyapatite can contribute to acceleration of the crystallization of PDO polymer ("Poly(para-Dioxanone)/Inorganic Particle Composites as a Novel Biomaterial"; Bai et al.: Journal of Biomedical Materials Research Part B: Applied Biomaterials, 945-951 and "Heterogeneous nucleation and self-nucleation of poly(p-dioxanone); Sabino et al.: Journal of Materials Science 35 (2000) 5071-5084).

U.S. Pat. No. 4,444,927 also discloses the use of sucrose or lactose as a nucleating agent for use in a production process (injection molding) for moldings made from polydioxanone.

In medical technology, suture materials based on polydioxanone colored by a dye to improve their handling properties (visualization in the surgical area) are used. Suture materials of this kind are commercially available, for example, under the MonoPlus® (B. Braun Aesculap), PDS II® (Ethicon) or vetsuture PDX® (Vetsuture) names. In PDS II, the colored suture materials have a higher degradation resistance compared to the uncolored suture materials, which may also be desirable depending on the indication.

With regard to particular indications, for example, in the field of cosmetic surgery, especially in face-lifting, but also in the closure of cutaneous and subcutaneous wounds, it is more advantageous, however, to use uncolored suture materials since a tattooing effect resulting from the use of colored suture materials cannot be ruled out. Nevertheless, even in treatment of such indications, there is also a need for suture materials having a retarded degradation profile. In patients having a known allergy to the dye used too, the choice of an uncolored suture material is indicated.

It could therefore be helpful to provide a composition, a molding, a thread, a medical kit and a medical product which very substantially avoid the shortcomings of the prior art and especially take account of the items above.

SUMMARY

We provide a composition including polydioxanone and/or a copolymer thereof and at least one carboxylic salt.

We also provide a molding including the composition.

We further provide a medical thread including the composition.

We still further provide a medical set including at least one needle and at least one thread.

We yet further provide a medical product including the composition.

DETAILED DESCRIPTION

Our compositions comprise polydioxanone (poly-paradioxanone or PDO) and/or a copolymer thereof. The compositions also comprise at least one carboxylic salt.

The expression "copolymer" means a polymer which, as well as para-dioxanone, is formed from at least one further monomer component. The term "copolymer" may therefore encompass bipolymers, tripolymers, tetrapolymers, especially with random or segmented distribution of the monomers, or the like.

The expression "at least one carboxylic salt" means a carboxylic salt or a plurality of, i.e. two or more, different carboxylic salts.

We surprisingly found:

Particularly advantageously, the composition is notable for a slowed or retarded degradation profile (breakdown profile), preferably based on hydrolysis.

This is probably attributable to increased formation of smaller crystallites or smaller spherulites in the composition or the polymer (PDO and/or copolymer thereof), the result of which is that crystallization is more homogeneous and accelerated overall. As a result of the higher number of crystallites and spherulites, and the formation thereof in smaller dimensions, the aqueous degradation medium appears to be able to penetrate into the composition only more slowly and in a more spatially limited manner, which slows the degradation rate. In this respect, the at least one carboxylic salt can also be regarded as a nucleating agent.

Thus, the composition is also suitable as a starting material for the production of moldings, especially in the form of medical products, for example, surgical threads or suture materials, nerve guidance conduits, meshes, stents and stent grafts or injection-molded articles, for example, staples, clips or vascular occlusion plugs, having retarded degradation characteristics.

For example, threads which have been produced from the composition, even after storage in Sorensen's buffer for several weeks, exhibit a knot pull tensile strength (KPTS) and linear tensile strength (LTS) that are each much higher than in threads that did not include any carboxylic salt, and this difference is greater in uncolored threads compared to colored threads.

The composition additionally features good handling properties, especially processing properties. For instance, the composition, for example, after extrusion and especially further processing steps, for example, a drawing operation, has a residual monomer content and an inherent viscosity or a molecular weight comparable to the residual monomer content and the inherent viscosity or the molecular weight of polydioxanone without a carboxylic salt. In other words, the at least one carboxylic salt, during the processing of the composition, for example, to give a thread, particularly advantageously does not induce any significant degradation of the polymer. This is manifested, for example, in the die pressures in the extrusion, which remain unchanged.

If the composition is extruded to give a molding, for example, a thread, a subsequent drawing operation particularly advantageously does not lead to any thread breaks. On top of that, the drawing can be conducted without significant deviations in the drawing ratios. In other words, the presence of the at least one carboxylic salt in the composition does not significantly impair the mechanical integrity of products, for example, threads produced from the composition, if at all, and promotes processibility.

If a thread is formed from the composition, it particularly advantageously features a smooth surface and flexible slackness which has been controlled from a medical point of view. The smooth surface having a low friction value especially facilitates atraumatic pulling of the thread through the tissue.

The at least one carboxylic salt, preferably is a metal salt, preferably an alkali metal and/or alkaline earth metal salt, of a carboxylic acid.

The at least one carboxylic salt is preferably selected from the group consisting of barium salt of a carboxylic acid, magnesium salt of a carboxylic acid, calcium salt of a carboxylic acid, strontium salt of a carboxylic acid and mixtures thereof.

Preferably, the at least one carboxylic salt is a colorless or non-coloring carboxylic salt. In principle, however, a colored or coloring carboxylic salt may also be an option.

The at least one carboxylic salt may also be the salt of an aliphatic and/or aromatic carboxylic acid.

More particularly, the at least one carboxylic salt may be the salt of a saturated or unsaturated carboxylic acid, especially one containing double and/or triple bonds.

In addition, the at least one carboxylic salt may be the salt of a branched or unbranched carboxylic acid.

It is preferable that the at least one carboxylic salt is the salt of an aliphatic, especially saturated, and preferably unbranched carboxylic acid.

The at least one carboxylic salt may be selected from the group consisting of fatty acid salt, amino acid salt, oxalic salt, salicylic salt, benzoic salt, nicotinic salt, resin acid salt and mixtures thereof.

It is particularly preferable when the at least one carboxylic salt is a fatty acid salt, preferably a salt of a saturated and especially unbranched fatty acid.

The fatty acid salt may in principle be a lower fatty acid, i.e. a fatty acid having 1 to 7 carbon atoms, middle fatty acid, i.e. a fatty acid having 8 to 12 carbon atoms, and/or a higher fatty acid, i.e. a fatty acid having more than 12 carbon atoms.

In principle, the fatty acid salt may be selected from the group consisting of formic salt, acetic salt, propionic salt, butyric salt, isobutyric salt, valeric salt, isovaleric salt, caproic salt, enanthic salt, caprylic salt, pelargonic salt, capric salt, undecanoic salt, lauric salt, tridecanoic salt, myristic salt, pentadecanoic salt, palmitic salt, oleic salt, linoleic salt, linolenic salt, margaric salt, stearic salt, nonadecanoic salt, arachic salt, behenic salt, lignoceric salt, cerotic salt and mixtures thereof.

Preferably, however, the at least one carboxylic salt is selected from the group consisting of lauric salt, myristic salt, palmitic salt, margaric salt, stearic salt and mixtures thereof.

Further preferably, the at least one carboxylic salt is an alkaline earth metal stearate, especially selected from the group consisting of barium stearate, magnesium stearate, calcium stearate, strontium stearate and mixtures thereof. Calcium stearate is preferable.

The at least one carboxylic salt may have a proportion of 0.1% to 10% by weight, especially 0.2% to 8% by weight, preferably 0.4% to 5% by weight, based on the total weight of the composition. A carboxylic acid content of 0.4% to 5% by weight is especially suitable for retarding or slowing degradation of the composition, which is preferably based on hydrolysis.

To suppress or reduce any matting effect attributable to the at least one carboxylic salt and/or to increase the transparency of the composition, a carboxylic acid content of 0.1% to 0.4%, based on the total weight of the composition, may be advantageous.

Preferably, the at least one carboxylic salt is present in the para-dioxanone and/or the copolymer.

More preferably, the polydioxanone and/or the copolymer thereof has been provided, additized or compounded with the at least one carboxylic salt.

Advantageously, the at least one carboxylic salt is distributed homogeneously or essentially homogeneously within the composition, especially within the polydioxanone and/or the copolymer. In other words, it is preferable when no significant local concentration differences and/or agglomerates exist in relation to the at least one carboxylic salt.

The copolymer may be a random copolymer, segmented copolymer or block copolymer.

Preferably, the copolymer is formed principally from para-dioxanone. For example, the para-dioxanone may have a proportion of at least 55%, especially 60% to 98%, preferably 70% to 95%, based on the total number of the monomer units present in the copolymer.

As well as para-dioxanone, the copolymer is preferably formed from at least one further monomer component, preferably absorbable monomer component. This monomer component may be selected from the group consisting of glycolide, lactide, ε-caprolactone, trimethylene carbonate, hydroxybutyrate, especially 3-hydroxybutyrate and/or 4-hydroxybutyrate, and combinations thereof.

In addition, the copolymer, as well as para-dioxanone, may be formed from ethylene glycol and/or diethylene glycol.

The copolymer may especially include polyethylene glycol units, especially in the form of blocks.

Preferably, the polydioxanone or copolymer thereof forms the main constituent of the composition. The expression "main constituent" means a polydioxanone content or copolymer content of at least 50% by weight, based on the total weight of the composition.

The polydioxanone or copolymer thereof may have a proportion of 50% to 99.9% by weight, preferably 65% to 99.8% by weight, more preferably 80% to 99.8% by weight, based on the total weight of the composition.

The composition may further include additives. Suitable additives may be selected from the group consisting of fillers, especially inorganic fillers, x-ray contrast agents, antimicrobial compounds, polymers, chemical and/or physical blowing agents and mixtures of these additives.

Examples of suitable fillers may be selected from the group consisting of calcium carbonate, β-tricalcium phosphate, calcium sulfate, hydroxyapatite and mixtures thereof.

Examples of antimicrobial compounds may be selected from the group consisting of guanidines, especially polyhexamethylenebiguanide (PHMB), metals or metal salts, for example silver or silver salts, antibiotics and mixtures thereof.

Chemical and/or physical blowing agents may generally be of interest for production of foam structures, for example, with regard to injection molding applications of the composition. Suitable physical blowing agents are especially propellant gases, for example, dinitrogen monoxide, carbon dioxide, oxygen, nitrogen or the like. Suitable chemical blowing agents are mixtures of carbonate and hydrogencarbonate salts, preferably of alkali metals and alkaline earth metals, especially in combination with citric acid and/or salts thereof (passive chemical blowing agents).

Useful contrast agents include especially x-ray contrast agents, for example, barium sulfate.

Supplementarily or alternatively, the composition includes, as an additive, an absorbable or at least water-soluble homopolymer, copolymer or terpolymer different than polydioxanone (PDO) and preferably the copolymer thereof. The composition may especially be present as a compatible or incompatible polymer mixture (blend).

The composition may also not include any further polymers or not be formed from any further polymer aside from the polydioxanone and/or copolymer thereof.

The composition may consist of polydioxanone or a copolymer thereof and the at least one carboxylic salt and optionally one or more additives. With regard to suitable additives, reference is made to the additives described above. More particularly, the composition may consist of one of the material combinations or mixtures described above.

The composition may, especially after a shaping step, for example, extrusion and especially after a subsequent aftertreatment, for example, drawing have a residual monomer content of 0.5% to 6%, especially of not more than 3%, preferably of not more than 2%, more preferably of not more than 1.2%.

In addition, the composition may have an inherent viscosity of 0.7 to 2.2 dl/g, especially 1.0 to 2.0 dl/g, preferably 1.2 to 1.8 dl/g. The viscosity values are based on the measurement of the viscosity of a hexafluoroisopropanol (HFIP) solution containing the composition in a concentration of 0.5% by weight, at a temperature of 30° C. by an 0a viscometer.

We also provide a molding comprising our composition or consisting of such a composition. The molding may be a semifinished product, finished product or end product.

The molding may have anchoring structures on its surface for anchoring in human or animal tissue, especially in the form of barbs or of the barb type. The anchoring structures preferably take the form of incisions into the molding surface. Additionally or alternatively, the anchoring structures may also be formed by means of perforations. The incisions and/or perforations (from which the anchoring structures form) are preferably made in the undrawn state of the molding. A subsequent drawing operation shapes the anchoring structures in a particularly advantageous manner, and especially lines them up. The anchoring structures especially allow the performance of wound closures and/or bone and/or organ fixations.

With regard to further features and advantages, especially in terms of the composition, unnecessary repetition is avoided by referring to the description so far in full.

We further provide a thread, especially a medical thread, preferably surgical thread or a surgical suture material. The thread or the suture material comprises our composition or consists of such a composition.

The thread may especially include no further polymers or be formed from no further polymer aside from the polydioxanone and/or copolymer thereof.

The thread may take the form of a monofil, pseudomonofil or multifil, especially braided, thread.

In addition, the thread may have anchoring structures on its surface for anchoring in human or animal tissue, especially in the form of barbs or of the barb type. The anchoring structures preferably take the form of incisions into the thread surface. Additionally or alternatively, the anchoring structures may also be formed by perforations. The incisions and/or perforations (which form the anchoring structures) are preferably made in the undrawn state of the thread. A subsequent drawing operation shapes the anchoring structures in a particularly advantageous manner and especially lines them up. The anchoring structures especially allow the performance of wound closures and/or bone and/or organ fixations. The expression "drawing" is generally understood in textile technology to mean a process step in the production of synthetic fibers in which the polymer chains, which are generally present in unordered and entangled form in the spun fiber, are oriented, generally with an increase in crystallization, by passing the undrawn spun fiber over a drawing system comprising a plurality of rolls (godets), the second roll generally having a greater peripheral speed than the first roll. In addition, elements of the drawing system may be heatable to heat the thread to above its glass transition point and to draw it in this state. In the course of drawing, a decrease in the diameter generally takes place, approximately by a factor of the square root of the drawing ratio. The strength of the drawn thread is normally several times higher and the elongation at break thereof is normally several times lower than that of the spun thread. The drawing can be effected in one or more stages. At the end thereof, either fixing or else relaxing is possible.

In addition, the thread may have a circular or non-circular, for example oval or polygonal, cross section.

The thread may have a thread thickness selected from the group consisting of USP 11-0 (0.010-0.019 mm), USP 10-0 (0.020-0.029 mm), USP 9-0 (0.030-0.039 mm), USP 8-0 (0.040-0.049 mm), USP 7-0 (0.050-0.069 mm), USP 6-0 (0.070-0.099 mm), USP 5-0 (0.100-0.149 mm), USP 4-0 (0.150-0.199 mm), USP 3-0 (0.200-0.249 mm), USP 2-0 (0.300-0.339 mm), USP 0 (0.350-0.399 mm), USP 1 (0.400-0.499 mm), USP 2 (0.500-0.599 mm), USP 3/4 (0.600-0.699 mm) and USP 5 (0.700-0.799 mm) (table of synthetic absorbable suture materials from USP 35).

Preferably, the thread has a thread thickness between USP 6-0 and USP 2.

The thread may have a core-shell structure. In this case, the composition may be present in the core and/or shell, or the core and/or shell may consist of the composition.

However, it is preferable when the composition is present only in the shell, or only the shell of the thread consists of the composition. In this way, the mechanical integrity of the thread core remains entirely unaffected.

Alternatively, the thread has an "islands-in-the-sea" structure, in which case the "sea" regions of the thread preferably comprise or consist of the composition.

With regard to further features and advantages of the thread, especially with regard to the composition, of the polydioxanone and/or copolymer thereof, of the at least one carboxylic salt and/or any additives, reference is likewise made in full to the description so far.

We also also provide a medical set, especially a surgical set, comprising at least one, especially one, needle and at least one, especially one, thread.

With regard to further features and advantages of the set, especially with regard to the thread and/or the composition, reference is likewise made in full to the description so far.

Finally, we provide a medical product comprising a composition or consisting of such a composition. Alternatively, the product may comprise at least one thread, especially a multitude of threads (i.e. two or more threads) or consist of at least one such thread or a multitude of such threads.

The medical product is preferably a surgical implant.

In addition, the medical product is preferably a textile implant, especially two- or three-dimensional textile implant.

The medical product may take the form of a flat structure, especially of a textile flat structure, or of a hollow prosthetic structure, especially textile hollow prosthetic structure. The hollow prosthetic structure is also preferably in the form of a hose, tube or cylinder.

The medical product may have a textile structure preferably selected from the group consisting of woven fabric, loop-formed knitted fabric, especially warp-knitted fabric, braid, loop-drawn knitted fabric and combinations thereof.

Alternatively, the medical product may have a nonwoven structure, preferably selected from the group consisting of spunbonded nonwoven, staple fiber web nonwoven, sprayed fiber web nonwoven, meltblown nonwoven, electrospun nonwoven or centrifuge-spun nonwoven.

The medical product may also have a non-textile structure and take the form, for example, of a film, membrane, especially capillary membrane, hose or the like.

The medical product may also take the form of a mesh, preferably medical mesh, more preferably surgical mesh.

For example, the medical product may be selected from the group consisting of hernia mesh, prolapse mesh and incontinence mesh.

In addition, it may be preferable when the medical product takes the form of a prosthesis, especially endoprosthesis, for example vessel prosthesis, stent or stent graft.

In addition, the medical product may, be a surgical staple, a surgical clip, a surgical anchor, especially bone anchor, or a vascular occlusion plug.

With regard to further features and advantages, especially in terms of the composition and/or the at least one thread, reference is likewise made in full to the preceding description.

Further features and advantages are elucidated in the form of examples. In each case, individual features can be implemented alone or in combination with one another.

EXAMPLES

The monofilaments cited are in most cases classified in terms of diameter with respect to the USP classes as the industry standard.

Example 1

Production of an Unadditized Monofilament Colored with D&C Violet 2 and of Thickness USP 3-0 (Comparative Example 1)

A PDO homopolymer having an inherent viscosity of 1.67 dl/g and a dye content of 0.091 wt % was used. The monomer content (NMR 300 MHz from Bruker; $CDCl_3$) prior to drying was 1.6 mol %. The polymer was dried at a temperature of 80° C. in a vacuum drying cabinet at 3 mbar for 18 h and then transferred under a nitrogen atmosphere to a pellet bottle. This bottle was placed onto the intake zone of a single-screw extruder having two heating zones via an adapter. Connected to the extruder via a flange was a spinning head with a 4×0.25 $cm^3$/rev. spinning pump, provided with a 4 to 2 adapter. The spinnerets used had a diameter of 1.0 mm with L/D=4. After leaving the spinneret, the extruded strand passed first through an air gap of 3-5 cm and then through a cooling bath (T=20°). After it had been drawn off by means of a pair of godets, the spun thread was wound up.

The extrusion parameters were as follows:
Temperature of extruder zone 1: 140° C.
Temperature of extruder zone 2: 160° C.
Temperature of spinning head: 180° C.
Spinning pump: 5.5 rpm
Draw-off rate: 7.0 m/min The spun thread had a diameter of 0.686 mm and a monomer content of 1.8%. The die pressure in the extrusion was 63 bar and the inherent viscosity was 1.54 dl/g.

The drawing was effected on a line consisting of a pair of feed godets, drawing oven, septet, drawing oven, septet and winder.

At a feed rate of 5 m/min, the temperature in the first drawing oven was 80° C. and that in the second drawing oven 95° C., the main drawing ratio in stage 1 was 5.3 and the overall drawing ratio was 5.6. The neck point was stable at the feed godet and no thread breaks occurred. The diameter of the drawn thread 1-1 was 0.297 mm±0.003 mm, and the thread surface was absolutely smooth. After an aftertreatment step for fixation and demonomerization, the monomer content was 0.6 mol %. The mechanical properties of the monofilament are shown in Table 1.

Example 2

Production of an Unadditized, Uncolored Monofilament of Thickness USP 3-0 (Comparative Example 2)

The extrusion of the uncolored PDO polymer having a viscosity of 1.65 dl/g and a monomer content of 1.8 mol % was effected analogously to Example 1.

The spun thread had a diameter of 0.684 mm and a monomer content of 2.0%. The die pressure in the extrusion was 61 bar and the inherent viscosity of the spun thread was 1.52 dl/g.

Drawing was commenced with the parameters from Example 1. In the course of this, we found that the drawing point moved away from the feed godet into the drawing oven 1, but also came out of the oven again a bit from time to time, which is an indication of a non-constant thread tension over time. The surface of the monofilament 2-1 thus obtained had rough sites, and irregularities in the diameter were clearly perceptible. The diameter was 0.296 mm±0.011 mm. No thread break occurred with these settings.

To minimize variations in diameter, eliminate the rough sites and localize the neck point at the feed godet, it was necessary to increase the main drawing ratio in stage 1 to 5.9 and the overall drawing ratio to 6.1. The diameter of the monofilament 2-2 was 0.277 mm±0.005 mm. As a result of the increase in the drawing ratio, there was an increase in the ovality of the monofil from 0.003 mm to 0.021 mm. After a run time of only three minutes, the first thread break occurred. After starting up again, this was repeated at intervals of 2-10 minutes. A reduction in the drawing ratio did not bring any improvement in this situation, as long as the neck point was kept at the feed godet. On further reduction toward the drawing ratios of Example 1, the neck point began to move again with formation of rough sites and variations in diameter.

After an aftertreatment step for fixation and demonomerization, the monomer content was 0.5 mol %. The mechanical properties of the monofilaments 2-1 and 2-2 are shown in Table 1.

Example 3

Production of a Colored Monofilament Additized with 0.07 Wt % of Calcium Stearate and of Thickness USP 3-0

The calcium stearate CPR-2-V from Greven (Germany) and the PDO polymer from example 1 were used. The additive (0.7 g) was added to 1000 g polymer and then distributed with maximum homogeneity therein by agitating and tumbling. This was followed by drying and extrusion as described in Example 1.

The spun thread had a diameter of 0.684 mm and a monomer content of 1.8%. The die pressure in the extrusion was 61 bar and the inherent viscosity of the spun thread was 1.52 dl/g. This shows that no degradation of the polymer took place in the extruder as a result of the additive.

The drawing and aftertreatment were effected under the conditions of Example 1. No thread breaks occurred, and the neck point was stable at the feed godet. The diameter of the drawn thread 3-1 was 0.296 mm±0.004 mm. The thread surface was absolutely smooth and felt somewhat softer compared to Example 1, which is possibly because of reduced surface friction as a result of the addition of fatty acid salt. After an aftertreatment step for fixation and demonomerization, the monomer content was 0.5 mol %. The mechanical properties of the monofilament 3-1 are shown in Table 1.

Example 4

Production of a Colored Monofilament Additized with 0.40 Wt % of Calcium Stearate and of Thickness USP 3-0

The production of the monofilament and the use of the materials required therefor corresponded to Example 3, except using 4.0 g of calcium stearate, based on 1000 g of PDO polymer.

The spun thread had a diameter of 0.684 mm and a monomer content of 1.7%. The die pressure in the extrusion was 62 bar and the inherent viscosity of the spun thread was 1.50 dl/g. This shows that no increased degradation of the polymer took place in the extruder as a result of the higher concentration of additive.

The drawing and aftertreatment were effected under the conditions of Example 1. No thread breaks occurred, and the neck point was stable at the feed godet. The diameter of the drawn thread 3-1 was 0.296 mm±0.003 mm. The thread surface was absolutely smooth and felt somewhat softer compared to example 1, which is probably because of reduced surface friction as a result of the addition of fatty acid salt. After an aftertreatment step for fixation and demonomerization, the monomer content was 0.6 mol %. The mechanical properties of the monofilament 4-1 are shown in Table 1.

Example 5

Production of an Uncolored Monofilament Additized with 0.07 Wt % of Calcium Stearate and of Thickness USP 3-0

1000 g of the uncolored polymer from example 2 were admixed with 0.7 g of calcium stearate as described in Example 3 and extruded.

The spun thread had a diameter of 0.685 mm and a monomer content of 1.8%. The die pressure in the extrusion was 59 bar and the inherent viscosity of the spun thread was 1.50 dl/g.

Surprisingly, compared to the unadditized uncolored PDO from Example 2, we found that the neck point under the standard drawing conditions of Example 1 was constantly at the feed godet, and so no increase in the drawing ratio was necessary. Also, in contrast to Example 2-1, there was no occurrence of rough sites or variations in diameter or, in contrast to Example 2-2, of thread breaks or any significant ovality. As an experiment, the drawing ratio in stage 1 was lowered from 5.3 to 5.1. Due to the addition of calcium stearate, the neck point nevertheless remained stable at the feed godet.

The diameter of the drawn thread 5-1 was 0.295 mm±0.004 mm. The thread surface was absolutely smooth and felt somewhat softer compared to Example 2, which is probably because of reduced surface friction as a result of the addition of fatty acid salt. After an aftertreatment step for fixation and demonomerization, the monomer content was 0.5 mol %. The mechanical properties of the monofilament 5-1 are shown in Table 1.

Example 6

Production of an Uncolored Monofilament Additized with 0.40 Wt % of Calcium Stearate and of Thickness USP 3-0

The production of the monofilament and the use of the materials required therefor corresponded to Example 5, except using 4.0 g of calcium stearate, based on 1000 g of PDO polymer.

The spun thread had a diameter of 0.684 mm and a monomer content of 1.9%. The die pressure in the extrusion was 58 bar and the inherent viscosity of the spun thread was 1.48 dl/g.

As in Example 5, we found that, surprisingly, the neck point under the standard drawing conditions of Example 1 was constantly at the feed godet, and so no increase in the drawing ratio was necessary. Also, in contrast to Example 2-1, there was no occurrence of rough sites or variations in diameter or, in contrast to Example 2-2, of thread breaks or any significant ovality. As an experiment, the drawing ratio in stage 1 here too was lowered from 5.3 to 5.0. Due to the increased addition of calcium stearate, the neck point nevertheless remained stable at the feed godet.

The diameter of the drawn thread 6-1 was 0.295 mm±0.003 mm. The thread surface was absolutely smooth and felt softer compared to Example 2, which is probably because of reduced surface friction as a result of the increased addition of fatty acid salt. After an aftertreatment step for fixation and demonomerization, the monomer content was 0.6 mol %. The mechanical properties of the monofilament 6-1 are shown in Table 1.

Example 7

Production of an Uncolored Monofilament Additized with 1.00 Wt % of Calcium Stearate and of Thickness USP 3-0

The production of the monofilament and use of the materials required therefor corresponded to Example 5, except using 10.0 g of calcium stearate, based on 1000 g of PDO polymer.

The spun thread had a diameter of 0.685 mm and a monomer content of 1.7%. The die pressure in the extrusion was 63 bar and the inherent viscosity of the spun thread was 1.52 dl/g.

As in Example 5, we found that, surprisingly, the neck point under the standard drawing conditions of Example 1 was constantly at the feed godet, and so no increase in the drawing ratio was necessary. Also, in contrast to Example 2-1, there was no occurrence of rough sites or variations in diameter or, in contrast to Example 2-2, of thread breaks or any significant ovality. As an experiment, the drawing ratio in stage 1 here too was lowered from 5.3 to 5.0. Due to the increased addition of calcium stearate, the neck point nevertheless remained stable at the feed godet. An experimental increase in the main drawing ratio from 5.3 to 5.9 also proceeded without thread breakage, but with an increase in ovality.

The diameter of the drawn thread 7-1 was 0.294 mm±0.003 mm. The thread surface was absolutely smooth and felt much softer compared to Example 2, which is probably because of reduced surface friction or else because of reduced flexural stiffness as a result of the increased addition of fatty acid salt. After an aftertreatment step for fixation and demonomerization, the monomer content was 0.5 mol %. The mechanical properties of the monofilament 7-1 are shown in Table 1.

TABLE 1

| Example | CaSt [%] | KPTS [N/mm$^2$] | LTS [N/mm$^2$] | Elongation at break [%] |
|---|---|---|---|---|
| 1-1 (v) | 0.00 | 323 | 520 | 43.7 |
| 2-1 (u) | 0.00 | 269 | 396 | 71.2 |
| 2-2 (u) | 0.00 | 298 | 470 | 35.3 |
| 3-1 (v) | 0.07 | 325 | 512 | 44.6 |
| 4-1 (v) | 0.40 | 376 | 491 | 45.2 |
| 5-1 (u) | 0.07 | 321 | 467 | 42.0 |
| 6-1 (u) | 0.40 | 352 | 516 | 41.8 |
| 7-1 (u) | 1.00 | 387 | 505 | 44.0 |

Mechanical Properties of the PDO Monofilaments USP 3-0 (v)=violet (u)=uncolored KPTS=knot pull tensile strength LTS=linear tensile strength Example 1-1 corresponds essentially to commercially available, violet-colored surgical suture materials such as PDS II® (Ethicon) or MonoPlus® (B. Braun Aesculap).

As Table 1 shows, the mechanical properties of the uncolored monofilaments without additive are unsatisfactory compared to the violet industry standard 1-1 (v).

Additional factors are the poor drawability of 2-2 (u) and the frequent occurrence of thread breaks. This problem was surprisingly solved by addition of calcium stearate, and an increase in knot pull tensile strength compared to the industry standard was also achieved in the case of violet polymer. The clearest improvements occurred in the case of uncolored monofils with rising additive content, which therefore also meet the strength requirements of the EP and USP.

Example 8

In Vitro Degradation Tests on the Monofilaments from Examples 1-7

In the context of absorbable materials, degradation is understood to mean loss of mechanical strength. To measure the degradation profile, a buffer solution consisting of potassium dihydrogenphosphate (13.14 mmol/l) and disodium hydrogenphosphate (53.5 mmol/l) with pH=7.4 was made up. The monofilaments (n=7) which had previously been cut to size were stored in this buffer solution at 37° C. for 4 weeks. Subsequently, the mechanical strength thereof was again determined as retention (percentage retention) of the original tensile strengths.

The values measured are shown in Table 2.

TABLE 2

| | | After pH 7.4 degradation at 37° C. for 4 weeks | | |
|---|---|---|---|---|
| Example | CaSt [%] | KPTS retention [%] | LTS retention [%] | Elongation at break [%] (absolute value) |
| 1-1 (v) | 0.00 | 74 | 69 | 21 |
| 2-2 (u) | 0.00 | 11 | 12 | 2 |
| 3-1 (v) | 0.07 | 83 | 78 | 22 |
| 4-1 (v) | 0.40 | 86 | 82 | 24 |
| 5-1 (u) | 0.07 | 14 | 23 | 4 |
| 6-1 (u) | 0.40 | 52 | 49 | 19 |
| 7-1 (u) | 1.00 | 75 | 73 | 23 |

Results of the Degradation Test: 4 Weeks at pH 7.4 and 37° C.

The results from the degradation test show that, even violet material, starting from a high retention level, the degradation rate can be reduced by addition of small concentrations of calcium stearate and hence the degradation behavior can be retarded.

This effect is manifested particularly clearly uncolored material: whereas the uncolored monofil without additive had virtually no strength after 4 weeks and had become extremely brittle, the degradation behavior could be improved even beyond the violet industry standard with rising additive content between 0.07 and 1.00 wt %.

Example 9

Determination of the Flexural Modulus of the Monofilaments from Examples 1-7

The flexural modulus of the monofilaments was determined on a flexural strength tester from Franckh (Germany) under standard climatic conditions with a clamped length of 5 mm and a bending angle of 30°. The flexural modulus was calculated from the flexural stiffness using the moment of inertia of cylindrical bodies. The results are shown in Table 3.

TABLE 3

| Example | CaSt [%] | Flexural modulus [N/mm²] |
|---------|----------|--------------------------|
| 1-1 (v) | 0.00 | 1589 |
| 2-2 (u) | 0.00 | 1613 |
| 3-1 (v) | 0.07 | 1580 |
| 4-1 (v) | 0.40 | 1405 |
| 5-1 (u) | 0.07 | 1591 |
| 6-1 (u) | 0.40 | 1397 |
| 7-1 (u) | 1.00 | 1314 |

Flexural modulus of the PDO monofilaments USP 3-0

Here Too, we Found that the Flexural Modulus Both of the Violet and of the uncolored monofilaments decreases with rising calcium stearate content, which constitutes an important criterion for monofil suture material since the handling properties when knotting and usually also the knot security rise as a result. In addition, a weaker memory effect on removal of the suture material from the packaging is to be expected.

Example 10

Production of an Uncolored Monofilament Additized with 1.00 Wt % of Calcium Stearate and of Thickness USP 2

A PDO homopolymer having an inherent viscosity of 1.58 dl/g and a monomer content of 1.6 mol % was used. The polymer was dried at a temperature of 80° C. in a vacuum drying cabinet at 3 mbar for 20 h and then transferred under a nitrogen atmosphere to a pellet bottle. This bottle was placed onto the intake zone of a single-screw extruder having two heating zones via an adapter. Connected to the extruder via a flange was a spinning head with a 4×0.25 cm³/rev. spinning pump, provided with a 4 to 2 adapter. The spinnerets used had a diameter of 2.0 mm with L/D=4. After leaving the spinneret, the extruded strand passed first through an air gap of 3 cm and then through a cooling bath (T=20°). After it had been drawn off by a pair of godets, the spun thread was wound up.

The extrusion parameters are as follows:
Temperature of extruder zone 1: 130° C.
Temperature of extruder zone 2: 160° C.
Temperature of spinning head: 180° C.
Spinning pump: 15.8 rpm
Draw-off rate: 5.0 m/min The spun thread had a diameter of 1.316 mm and a monomer content of 1.2%. The die pressure in the extrusion was 75 bar.

The drawing was effected on a line consisting of a pair of feed godets, drawing oven, septet, drawing oven, septet and winder.

At a feed rate of 5 m/min, the temperature in the first drawing oven was 95° C. and that in the second drawing oven 115° C., and the main drawing ratio in stage 1 was 5.3, as was the overall drawing ratio, since the 2nd stage was merely a fixing stage. The neck point was stable at the feed godet and no thread breaks occurred. The diameter of the drawn thread 8-1 was 0.595 mm±0.005 mm, and the thread surface was absolutely smooth. After an aftertreatment step for further fixation and demonomerization, the monomer content was 0.5 mol %. The mechanical properties, and the retention of knot pull tensile strength after degradation in phosphate buffer with pH 7.4 at 37° C. for 4 weeks, of the monofilament are shown in Table 4.

Example 11

Production of an Uncolored Monofilament Additized with 0.40 Wt % of Calcium Stearate and of Thickness USP 5-0

A PDO homopolymer having an inherent viscosity of 1.58 dl/g and a monomer content of 1.6 mol % was used. The polymer was dried at a temperature of 80° C. in a vacuum drying cabinet at 3 mbar for 20 h and then transferred under a nitrogen atmosphere to a pellet bottle. This bottle was placed onto the intake zone of a single-screw extruder having two heating zones via an adapter. Connected to the extruder via a flange was a spinning head with a 4×0.25 cm³/rev. spinning pump. The extrusion was carried out at four points. The spinnerets used had a diameter of 0.5 mm with L/D=4. After leaving the spinneret, the extruded strands passed first through an air gap of 8 cm and then through a cooling bath (T=) 20°. After they had been drawn off by means of a pair of godets, the spun threads were wound up.

The extrusion parameters were as follows:
Temperature of extruder zone 1: 140° C.
Temperature of extruder zone 2: 160° C.
Temperature of spinning head: 180° C.
Spinning pump: 5.5 rpm
Draw-off rate: 10.0 m/min The spun thread had a diameter of 0.390 mm and a monomer content of 1.6%. The die pressure in the extrusion was 73 bar.

The drawing was effected on a line consisting of a pair of feed godets, drawing oven, septet, drawing oven, septet and winder.

At a feed rate of 10 m/min, the temperature in the first drawing oven was 70° C. and that in the second drawing oven 80° C., the main drawing ratio in stage 1 was 5.2, and the total drawing ratio was 5.3. The neck point was stable at the feed godet and only one thread break occurred at a total production volume of about 15 000 m. The diameter of the drawn thread 9-1 was 0.172 mm±0.003 mm, and the thread surface was absolutely smooth. After an aftertreatment step for further fixation and demonomerization, the monomer content was 0.6 mol %. The mechanical properties, and the retention of knot pull tensile strength after degradation in phosphate buffer with pH 7.4 at 37° C. for 4 weeks, of the monofilament are shown in Table 4.

TABLE 4

| Example | USP | CaSt [%] | KPTS [N/mm²] | LTS [N/mm²] | Elongation at break [%] | KPTS ret. after 4 w [%] |
|---------|-----|----------|--------------|-------------|-------------------------|-------------------------|
| 8-1 (v) | 2 | 1.00 | 278 | 435 | 38.7 | 77 |
| 9-1 (u) | 5-0 | 0.40 | 419 | 538 | 43.2 | 59 |

Properties of Uncolored PDO Monofils USP 2 and USP 5-0

Table 4 demonstrates that additization with carboxylic salts can be performed even at low and high USP thicknesses, and likewise leads to the excellent results therein as were also surprisingly found that the moderate thickness USP 3-0 (Examples 1-7). It should be noted that, in the case of monofilaments, both the knot pull tensile strength and linear tensile strength, both based on the cross-sectional area of the monofil, decrease with increasing diameter. Example 8-1 listed in Table 4, an uncolored PDO monofil additized with carboxylic salt and of thickness USP 2, is somewhat better than the violet industry standard with regard to strengths and retention after degradation for four weeks.

Example 12

Production of an Uncolored Unadditized Barbed PDO Suture Material of Thickness USP 3-0 by Incision in the Undrawn State with Subsequent Drawing (Comparative Example 3)

Compared to the suture materials for conventional knotting (individual or continuous seam), self-anchoring systems (barbed sutures) have the advantage of saving time during operation and of a homogeneous stress profile in the wound, which minimize, for example, scarring and necrosis.

To produce a barbed thread, the extruded undrawn strand from Example 2 was cut to length 30 cm. Subsequently, the strand was provided, by way of a test, with 50 incisions, separated by 0.25 mm, into the middle section of the strand by a prototype cutting machine, with a cutting angle relative to the thread surface of 25° and a cutting depth in relation to the diameter of the strand of 30%. The incisions were each arranged offset by 120° relative to one another. This was followed by discontinuous drawing of the strand in a heated oven at 80° C. to a total drawing ratio of 3.5 to 4.3, in the course of which the barbs were to take shape and be lined up. While this was possible without any difficulty or thread breaks with the violet comparative material from Example 1, 8 out of 10 specimens broke here during drawing. Only through a further reduction in the drawing ratio to 2.8 did no thread break occur in 10 out of 10 samples, but the strength based on cross section was reduced by 45% compared to the threads formed from Example 1, which is unacceptable.

Example 13

Production of an Uncolored Barbed PDO Suture Material Additized with 0.4% Calcium Stearate and of Thickness USP 3-0 by Means of Incision in the Undrawn State and Subsequent Drawing To produce a barbed thread, the extruded undrawn strand from Example 6 was cut to length 30 cm. Subsequently, the strand was provided, by way of a test, with 50 incisions, separated by 0.25 mm, into the middle section of the strand by a prototype cutting machine, with a cutting angle relative to the thread surface of 25° and a cutting depth in relation to the diameter of the strand of 30%. The incisions were each arranged offset by 120° relative to one another. In contrast to Example 10, it was possible to discontinuously draw the strand provided with the incisions in a heated oven at 80° C. to a drawing ratio between 3.5 and 4.3 without occurrence of any thread break. The linear strength achieved was 5% higher than that of the thread formed from the violet strand from Example 1.

Example 14

Production of Injection Moldings from Uncolored PDO without and with 1.0% Added Calcium Stearate Using an Arburg Allrounder injection molding machine, with a specific mold for production of specimens, both rods having a length of 20 cm and a diameter of 1.0 mm and thin plaques having the dimensions of side length a=1 cm, side length b=10 cm and thickness d=1 mm were produced. For this purpose, the barrel was heated to 175° C. and the mold to 40° C. (maximum of the crystallization rate). The time from the injection of the melt into the mold to the ejection or to the removal of the molding was lowered, commencing at 150 s in intervals of 10 sec, until the molding could no longer be ejected or removed in a regular manner or the molding was still of such low dimensional stability that it deformed permanently in the process. This time was 70 s for the unadditized PDO, whereas only 30 s were needed for the likewise uncolored polymer additized with 1.0% carboxylic acid.

Example 15

Production of Surgical Moldings with Anchoring Structures from the Moldings without and with Added Carboxylic Salt With the prototype cutting machine, incisions as described in Example 13 were made into the rods having a diameter of 1.0 mm from Example 14. This was done using both rods without and with 1.0 wt % of added carboxylic salt. The rods provided with incisions were drawn as described in Example 13. An alternative drawing method involved clamping the ends of the rods provided with incisions in the clamps of a tensile tester and heating the region between the clamps to 80° C. with hot air and, after a heating time of 15 s, moving the clamps apart to result in a drawing ratio of 3.75. In both drawing methods, the break rate for the unadditized moldings was at least 75%, whereas the 1.0% additized moldings did not break in the course of drawing. In drawing operations without breaks, the anchoring structures took shape during the drawing and lined up.

Without restricting the possible uses, the moldings with anchoring structures thus produced can be used, for example, as absorbable, self-fixing bone pins, as suture material anchors, as self-fixing occlusion plugs for vessels, but also as surgical suture material.

With a small punching tool (shape of an open arrowhead) with side length a=3 mm and a tip angle of 75°, perforations separated by 8 mm were made into the plaques, at least in the middle of the plaques and over the entire thickness of the plaques. In every second plaque, perforations were additionally also made on the lateral edge of the plaque, such that anchoring structures formed here directly. This was done using plaques without and with 1.0 wt % added carboxylic salt.

The plaques thus provided with perforations were drawn as described in Example 13. An alternative drawing method involved clamping the ends of the plaques provided with perforations in the clamps of a tensile tester and heating the region between the clamps to 80° C. with hot air and, after a heating time of 15 s, moving the clamps apart to result in a drawing ratio of 3.75. In both drawing methods, the break rate for the unadditized moldings without lateral perforation was 60% and with lateral perforation was 90%, whereas the 1.0% additized moldings did not break in the course of drawing.

In drawing operations without breaks, the flat anchoring structures took shape and lined up in the middle of the plaque, with one portion projecting on the reverse side and another portion of the flat anchoring structures projecting on the front side of the plaques. The lateral anchoring structures which had likewise been punched out experienced additional shaping through the drawing operation.

The flat moldings having anchoring structures thus produced can, without restricting their use, for example, serve to fix organs or else bones in the manner of a cable tie. In addition, they can, for example, serve for lifting in cosmetic surgery, by virtue of having either bidirectional anchoring structures or unidirectional anchoring structures with a stopper or loop on an opposite side from the needle or from the insertion tip and being introduced into the tissue in a linear manner.

Quite generally, the anchoring or barb structures mentioned in the examples section, as well as the punching operation, can also be produced by mechanical incision, for example, by blades, by laser cutting, by thermal cutting, for example by means of a wire heated above the melting point of the polymer, or by injection molding methodology. The same also applies to the anchoring structures described in the general part of the description.

The above-described experimental results show the following:

The monomer content and the molecular weight (indicator: extrusion die pressure) of the extrudates were within the normal range. Thus, the added calcium stearate caused no significant degradation, if any, of the PDO polymer during extrusion.

In contrast to uncolored PDO polymer unadditized with carboxylic salt, the drawing could be conducted analogously to violet-colored PDO polymer, virtually without thread breaks and without any significant deviation in the process parameters.

The neck point during the drawing tests on the monofilaments, in spite of variation in the drawing ratios, was stable at the feed godet on additization with carboxylic salt.

The quality of the thread surface was assessed as good to very good. The addition of calcium stearate reduced the flexural stiffness by up to 17%.

The original tensile strengths, especially the knot pull tensile strength, which is important for surgical suture material, were increased through the additization with carboxylic salt compared to the violet industry standard, and distinctly increased compared to uncolored unadditized polymer. At the same time, the flexural modulus was reduced.

The retentions of the knot pull tensile strength and linear tensile strength of monofilaments of the inventive compositions were significantly enhanced compared to uncolored PDO monofilaments without addition of carboxylic salts.

The addition of 0.4 or more percent by weight of calcium stearate to the uncolored PDO achieved retentions of the knot pull tensile strength and linear tensile strength in the degradation test after 4 weeks of degradation time that, at 52%-77%, were at least close to or even better than that of the violet industry standard. In contrast, uncolored PDO monofilaments without calcium stearate showed only retentions of 10% to 15%.

In contrast to violet-colored PDO, it was not possible to find any unwanted traces of the additive on single-use surgical gloves after the inventive uncolored threads additized with carboxylic salt had been pulled through them once, whereas the violet suture material left a significant colored trace. Any tattooing effect can therefore be ruled out.

In the production of moldings in an injection molding process, the cycle time was significantly shortened through the addition of calcium stearate compared to uncolored PDO. The duration required between injection of the melt and ejection of the molding from the mold was reduced to less than half.

Moldings and threads made from uncolored PDO polymer with anchoring structures, especially when the incisions and/or perforations were made in the undrawn state, followed by drawing, were producible in sufficient strength and without thread breaks during drawing only after additization with carboxylic salt.

The invention claimed is:

1. Surgical suture material consisting of an uncolored composition including polydioxanone homopolymer and 0.4% to 5% by weight of at least one carboxylic salt based on the total weight of the composition.

2. The surgical suture material as claimed in claim 1, wherein the at least one carboxylic salt is a metal salt of a carboxylic acid.

3. The surgical suture material as claimed in claim 1, wherein the at least one carboxylic salt is selected from the group consisting of barium salt of a carboxylic acid, magnesium salt of a carboxylic acid, calcium salt of a carboxylic acid, strontium salt of a carboxylic acid and mixtures thereof.

4. The surgical suture material as claimed in claim 1, wherein the at least one carboxylic salt is selected from the group consisting of fatty acid salt, amino acid salt, oxalic salt, salicylic salt, benzoic salt, nicotinic salt, resin acid salt and mixtures thereof.

5. The surgical suture material as claimed in claim 1, wherein the at least one carboxylic salt is a salt of a saturated and unbranched fatty acid.

6. The surgical suture material as claimed in claim 1, wherein the at least one carboxylic salt is selected from the group consisting of lauric salt, myristic salt, palmitic salt, margaric salt, stearic salt and mixtures thereof.

7. The surgical suture material as claimed in claim 1, wherein the at least one carboxylic salt is an alkaline earth metal stearate.

8. A molding comprising the surgical suture material as claimed in claim 1.

9. The molding as claimed in claim 8, wherein anchoring structures are formed on the molding or within human or animal tissue, and the anchoring structures are formed by incisions and/or perforations in an undrawn state of the molding and take shape and are lined up by subsequently subjecting the molding to a drawing operation.

10. A medical thread comprising the surgical suture material as claimed in claim 1.

11. The thread as claimed in claim 10, wherein anchoring structures that enable anchoring within human or animal tissue are formed on the thread, the anchoring structures formed by incisions and/or perforations in an undrawn state of the thread and taking shape and being lined up by subjecting the thread to a subsequent drawing operation.

12. A medical set comprising at least one needle and at least one thread as claimed in claim 10.

13. A medical product comprising the surgical suture material as claimed in claim 1.

14. The medical product as claimed in claim 13, which is a textile structure selected from the group consisting of woven fabric, loop-formed knitted fabric, loop-drawn knitted fabric, braided fabric, nonwoven fabric and combinations thereof.

15. A medical product comprising at least one thread as claimed in claim 10.

16. Uncolored surgical suture material comprising a composition comprising polydioxanone homopolymer and 0.4% to 5% by weight of at least one carboxylic salt based on the total weight of the composition.

17. Surgical suture material consisting of an uncolored composition including polydioxanone homopolymer and 0.4% to 5% by weight of at least one carboxylic salt based on the total weight of the composition, wherein the at least one carboxylic salt is distributed homogeneously within the polydioxanone homopolymer.

* * * * *